(12) United States Patent
Lawrence

(10) Patent No.: US 7,557,209 B2
(45) Date of Patent: Jul. 7, 2009

(54) PROCESS FOR THE PREPARATION OF (1S,4R)-CIS-4-[2-AMINO-6-CHLORO-9H-PURIN-9-YL]-2-CYCLOPENTENE-1-METHANOL

(75) Inventor: Ronnie Maxwell Lawrence, Stevenage (GB)

(73) Assignee: Glaxo Group Limited, Greenford, Middlesex (GB)

( * ) Notice: Subject to any disclaimer, the term of this patent is extended or adjusted under 35 U.S.C. 154(b) by 520 days.

(21) Appl. No.: 10/570,229

(22) PCT Filed: Sep. 2, 2004

(86) PCT No.: PCT/EP2004/009819

§ 371 (c)(1),
(2), (4) Date: Feb. 28, 2006

(87) PCT Pub. No.: WO2005/023811

PCT Pub. Date: Mar. 17, 2005

(65) Prior Publication Data

US 2007/0027316 A1 Feb. 1, 2007

(30) Foreign Application Priority Data

Sep. 4, 2003 (GB) ................. 0320738.8

(51) Int. Cl.
*C07D 473/40* (2006.01)
(52) U.S. Cl. .................................. 544/277
(58) Field of Classification Search ............... 544/277
See application file for complete search history.

(56) References Cited

U.S. PATENT DOCUMENTS

| | | | | |
|---|---|---|---|---|
| 4,543,255 A | * | 9/1985 | Shealy et al. | 514/261.1 |
| 4,728,736 A | * | 3/1988 | Shealy et al. | 544/254 |
| 5,641,889 A | * | 6/1997 | Daluge et al. | 544/277 |
| 5,917,041 A | * | 6/1999 | Daluge et al. | 544/264 |

FOREIGN PATENT DOCUMENTS

| | | |
|---|---|---|
| EP | 0325460 | 10/1992 |
| EP | 0628044 | 12/1994 |
| EP | 0741710 | 11/1996 |
| EP | 0434450 | 7/1999 |
| WO | 95/21161 | 8/1995 |
| WO | WO95/21161 | 8/1995 |
| WO | 98/52949 | 11/1998 |
| WO | WO98/52949 | 11/1998 |
| WO | 99/19327 | 4/1999 |
| WO | WO99/19327 | 4/1999 |
| WO | 00/19327 | 4/2000 |

OTHER PUBLICATIONS

Evans, J. Chem. Soc., Perkin Trans. 1, 1992, 589-592.*
Berge et al., Pharmaceuticals Salts, J. of Pharm. Sci. 66(1):1-19 (1977).
Daluge et al., An Efficient, Scalable synthesis of the HIV Reverse Transcriptase Inhibitor Ziagen® (1592U89), Nucleosides, Nucleotides & Nucleic Acids 19:297-327 (2000).
Fleisher et al., Improved oral drug delivery: solubility limitations overcome by the use of prodrugs, Advanced Drug Delivery Reviews 19:115-130 (1996).
Higuchi and Stella, Pro-drugs as Novel Drug Delivery Systems, ACS Symposium Series 14, Amer. Chem. Soc., (Sep. 1974).
Legraverend et al., Synthesis of a New Series of Purine Derivatives and their Anti-Cyclin-Dependent Kinase Activities, J. Heterocyclic Chem. 38:299-303 (2001).
Pederson et al., Improved Glucose Tolerance in Zucker Fatty Rats by Oral Administration of the Dipeptidyl Peptidase IV Inhibitor Isoleucine Thiazolidide, Diabetes 47:1253-1258 (1998).
Vince and Hua, Synthesis and Anti-HIV Activity of Carbocyclic 2',3'-Didehydro-2',3'-dideoxy 2,6-Disubstituted Purine Nucleosides, J. Med. Chem. 33:17-21 (1990).
Berge et al., "Pharmaceutical Salts", J. of Pharm. Sci. Vol. 66(1), pp. 1-19, 1977.
Daluge et al., "An Efficient, Scalable synthesis of theh HIV Reverse Transcriptase Inhibitor Ziagen® (1592U89)", Nucleosides, Nucleotides & Nucleic Acids, vol. 19, pp. 297-327, 2000.
Fleisher et al., "Improved oral drug delivery: solubility limitations overcome by the use of prodrugs", Advanced Drug Delivery Reviews, vol. 19, pp. 115-130, 1996.
Legraverend et al., "Synthesis of a New Series of Purine Derivatives and their Anti-Cyclin-Dependent Kinase Activities", J. Heterocyclic Chem., vol. 38, pp. 299-303, 2001.
Pederson, et al., "Improved Glucose Tolerance in Zucker Fatty Rats by Oral Administration of the Dipeptidyl Peptidase IV Inhibitor Isoleucine Thiazolidide", Diabetes, vol. 47, pp. 1253-1258, 1998.
Vince and Hua,"Synthesis and Anti-HIV Activity of Carbocyclic 2',3'-Didehydro-2',3'-dideoxy 2, 6-Disubstituted Purine Nucleosides" J. Med. Chem., vol. 33, pp. 17-21, 1990.

* cited by examiner

Primary Examiner—Mark L Berch
(74) Attorney, Agent, or Firm—Karen L. Prus

(57) ABSTRACT

The present invention relates to a process for preparing a chloropurine compound of formula (I)

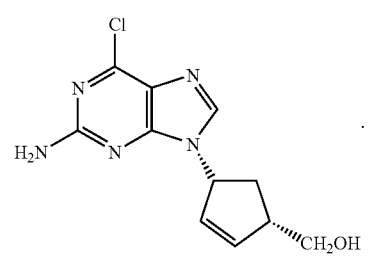

9 Claims, No Drawings

PROCESS FOR THE PREPARATION OF (1S,4R)-CIS-4-[2-AMINO-6-CHLORO-9H-PURIN-9-YL]-2-CYCLOPENTENE-1-METHANOL

CROSS-REFERENCE TO RELATED APPLICATIONS

This application is filed pursuant to 35 USC 371 as a U.S. National Phase Application of International Patent Application Serial No. PCT/EP2004/009819 filed on Sep. 2, 2004, which claims priority from 0320738.8 filed on Sep. 4, 2003 in the United Kingdom.

The present invention relates to a novel process for the preparation of a chloropurine compound of formula (I) or a derivative thereof.

BACKGROUND OF THE INVENTION (1S,4R)-cis-[2-Amino-6chloro-9H-purin-9-yl]-2-cyclopentene-1-methanol, the chloropurine compound of formula (I)

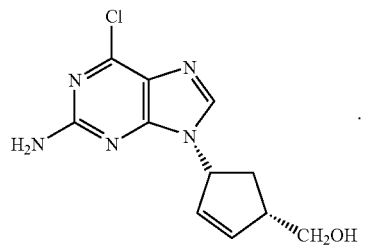

is described in European Patent No. 0 325 460 and can be used as an intermediate in the manufacture of abacavir ((1S,4R)-cis-4-[2-amino-6-(cyclopropylamino)-9H-purin-9-yl]-2-cyclopentene-1-methanol), a 2-aminopurine nucleoside compound of formula (II)

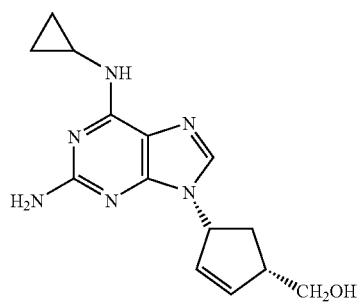

The antiviral use of abacavir, particularly in the treatment of the human immunodeficiency virus (HIV), is described in European Patent No. 0 434 450 and the hemisulfate salt of abacavir, described in International Patent Application No. WO98/52949, is commercially available from GlaxoSmithKdine for the treatment of HIV under the tradename ZIAGEN®.

Processes for preparing abacavir and intermediates useful in the synthesis of abacavir have been described by, for example, Daluge et al. in Nucleosides, Nucleotides & Nucleic Acids, 19 (1&2), 2000, 297-327. International Patent Application No. WO99/19327 describes an in situ process for the preparation of the chloropurine compound of formula (I) which comprises hydrolysing a compound of formula (III)

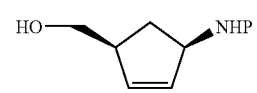

wherein P is a protecting group, in the presence of an acid, condensing the product of formula (IV) formed

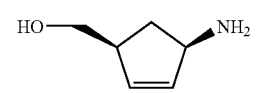

in situ in the presence of a base with a compound of formula (V)

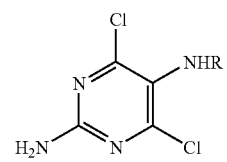

in which R represents CHO or H, followed by ring closure in situ of the resulting intermediate of formula (VI)

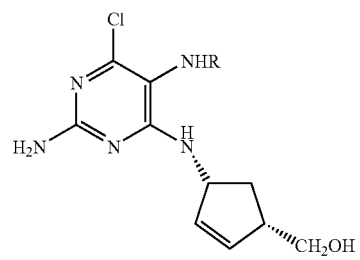

According to WO99/19327, the ring closure reaction is preferably carried out in the presence of from about 1.5 to 3 molar equivalents of hydrochloric acid and a large excess of triethylorthoformate, which results in precipitation of the hydrochloride salt of the chloropurine compound of formula (I).

As abacavir is sold as a prescription medicine for the treatment of HIV infections, there exists a need to develop more efficient processes for preparing the compound in large quantities.

We have now found a process for preparing the chloropurine compound of formula (I) or a derivative thereof in which the amount of both the acid and formate derivative used in the cyclisation step is significantly reduced. The process according to the present invention thus allows abacavir and derivatives thereof to be prepared without isolation of the highly toxic hydrochloride salt of the chloropurine compound of formula (I), which can be difficult to filter, and avoids the problems associated with handling gaseous hydrogen chloride. As a result, the process according to the present invention is a safer process in which the amount of solvent used is lowered, minimising waste and environmental impact, the cycle time is reduced, and the throughput and overall yield of the process is increased.

SUMMARY OF THE INVENTION

Accordingly, the present invention provides a process for preparing a chloropurine compound of formula (I)

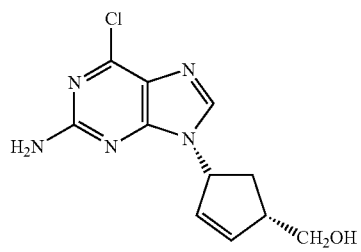

(I)

or a derivative thereof, which comprises ring closure of the compound of formula (VII) or a derivative thereof

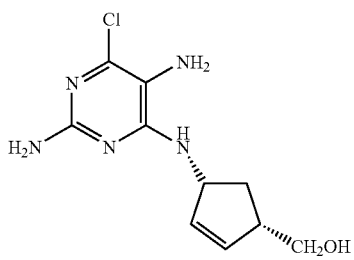

(VII)

in the presence of catalytic acid and at least one equivalent of a formate derivative.

DETAILED DESCRIPTION

Acids suitable for use in the process of the present invention include concentrated aqueous and anhydrous mineral acids, for example sulfuric acid, hydrochloric acid, or an alkyl or arylsulfonic acid. Preferably, the acid is sulfuric acid. In order to effect ring closure, the acid is present in a catalytic amount. Typically, the acid is present in an amount of up to 0.2 equivalents by mole based on the amount of the compound of formula (VII), for example up to 0.1 equivalents by mole. In one embodiment, the acid is present in an amount of from 0.05 to 0.1 equivalents. In another embodiment, the acid is present in an amount of from 0.01 to 0.05 equivalents. In a further embodiment, the acid is present in an amount of about 0.05 equivalents.

Formate derivatives suitable for use in the process of the present invention include trialkylorthoformates such as trimethylorthoformate or triethylorthoformate, and diethoxymethyl acetate. Preferably, the formate derivative is triethylorthoformate. In the process of the present invention, the formate derivative is present in an amount of at least one equivalent by mole based on the amount of the compound of formula (VII), preferably from 1 to 5 equivalents, more preferably from 1 to 2 equivalents and most preferably from 1 to 1.5 equivalents.

The ring closure reaction is preferably carried out in an anhydrous polar aprotic solvent, for example acetonitrile, anhydrous dimethylacetamide, dimethylformamide, or an alkanol solvent such as methanol, ethanol, n-butanol, isopropanol (IPA) or industrial methylated spirit (IMS), in particular n-butanol. The reaction mixture is generally heated to a temperature of from 20 to 100° C., preferably from 40 to 80° C. and more preferably from 60 to 70° C., for at least 3 hours.

The compound of formula (VII) may be prepared by condensing an amino alcohol of formula (IV) as hereinbefore defined or a derivative thereof with a compound of formula (VIII) or a derivative thereof

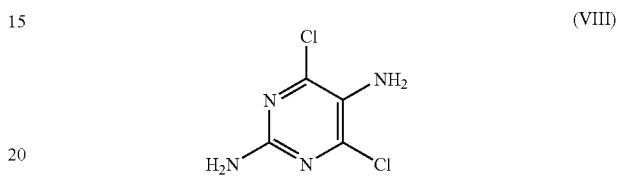

(VIII)

in the presence of a base.

The base is generally a trialkylamine such as triethylamine or an alkali metal carbonate or bicarbonate such as potassium or sodium carbonate or bicarbonate. Preferably, the base is an alkali metal bicarbonate such as potassium or sodium bicarbonate, in particular sodium bicarbonate. The base is present in an amount at least sufficient to neutralise the acid produced in the condensation reaction. Generally, there will be at least 2 equivalents by mole of base based on the amount of the compound of formula (IV), preferably from 2.2 to 5 equivalents, more preferably about 2.5 equivalents.

The condensation reaction between the compound of formula (IV) and the compound of formula (VIII) may be carried out under reflux in a polar solvent such as an alkanol, for example, methanol, ethanol, n-butanol, IPA or IMS, ethyl acetate or acetonitrile. Preferably, the condensation reaction is carried out in n-butanol. The reaction mixture is generally heated to a temperature of from 60 to 110° C., preferably from 80 to 110° C. and more preferably from 90 to 100° C., for at least 8 hours.

After the condensation reaction is complete, the reaction mixture may be diluted and filtered at a temperature of at least 70° C. In one embodiment, the reaction mixture is filtered through charcoal. The filtrate may be concentrated and used in the ring closure reaction without further purification.

In a preferred embodiment of the present invention, the condensation reaction is carried out in n-butanol in the presence of sodium bicarbonate. Preferably, once the condensation reaction is complete, the reaction mixture is diluted, filtered and then concentrated. In one embodiment, the volume of solvent is reduced by at least 50%, for example from 50 to 60%. In a further embodiment, the volume of solvent is reduced by at least 10%, for example from 10 to 30%.

In a further embodiment of the present invention, the condensation reaction is carried out in n-butanol in the presence of anhydrous potassium carbonate. The potassium carbonate removes the liberated water from solution thus avoiding the need for a concentration step.

The compound of formula (IV) may be prepared by the procedure described in WO99/19327 and the compound of formula (VIII) may be prepared by the procedure described in WO95/21161 and WO99/19327.

According to the process of the present invention, the ring closure reaction results in the formation of the chloropurine compound of formula (I) or a derivative thereof. As the acid used in the ring closure reaction is only present in a catalytic amount, the chloropurine compound does not precipitate out as a salt but remains in solution. Thus, the chloropurine compound can be converted in situ to abacavir or a derivative thereof.

In one embodiment, the chloropurine compound of formula (I) or derivative thereof is converted to abacavir or a derivative thereof by treatment of the reaction mixture with cyclopropylamine. The abacavir or derivative thereof may be isolated from the reaction mixture, for example by addition of glutaric acid to form the glutarate salt. The isolated abacavir or derivative thereof may then be converted to abacavir hemisulfate by, for example, the procedures described in WO98/52949.

When used herein, the term "pharmaceutically acceptable" means a derivative which is suitable for pharmaceutical use. Salts and solvates which are suitable for use in medicine are those wherein the counterion or associated solvent is pharmaceutically acceptable. However, salts and solvates having non-pharmaceutically acceptable counterions or associated solvents are within the scope of the present invention, for example, for use as intermediates in the preparation of other derivatives.

When used herein, the term "pharmaceutically acceptable derivative", means any pharmaceutically acceptable salt, solvate, or prodrug e.g. ester, which upon administration to the recipient is capable of providing (directly or indirectly) the compound, or an active metabolite or residue thereof. Such derivatives are recognizable to those skilled in the art, without undue experimentation. Nevertheless, reference is made to the teaching of Burger's Medicinal Chemistry and Drug Discovery, 5$^{th}$ Edition, Vol 1: Principles and Practice, which is incorporated herein by reference to the extent of teaching such derivatives. Preferred pharmaceutically acceptable derivatives are salts, solvates, esters, carbamates and phosphate esters. Particularly preferred pharmaceutically acceptable derivatives are salts, solvates and esters. Most preferred pharmaceutically acceptable derivatives are salts and esters, especially salts.

When used herein, the term "derivative", means any pharmaceutically acceptable derivative or non-pharmaceutically acceptable derivative which is suitable for use in the process of the present invention. The skilled person will appreciate that non-pharmaceutically acceptable derivatives may be used to prepare compounds and derivatives suitable for pharmaceutical use. In one embodiment, the derivatives used or prepared according to the present invention are pharmaceutically acceptable derivatives.

Compounds prepared using the process of the present invention may be in the form of and/or may be administered as a pharmaceutically acceptable salt. For a review on suitable salts see Berge et al., J. Pharm. Sci., 1977, 66, 1-19.

Typically, a pharmaceutically acceptable salt may be readily prepared by using a desired acid or base as appropriate. The salt may precipitate from solution and be collected by filtration or may be recovered by evaporation of the solvent.

Salts prepared using the process of the present invention may, for example, comprise acid addition salts resulting from reaction of an acid with a basic nitrogen atom. Salts encompassed within the term "pharmaceutically acceptable salts" refer to non-toxic salts of the compounds of this invention. Suitable addition salts are formed from acids which form non-toxic salts and examples are acetate, p-aminobenzoate, ascorbate, aspartate, benzenesulfonate, benzoate, bicarbonate, bismethylenesalicylate, bisulfate, bitartrate, borate, bromide, calcium edetate, camsylate, carbonate, chloride, clavulanate, citrate, cyclohexylsulfamate, dihydrochloride, edetate, edisylate, estolate, esylate, ethanedisulfonate, ethanesulfonate, formate, fumarate, gluceptate, gluconate, glutamate, glutarate, glycollate, glycollylarsanilate, hemisulfate, hexylresorcinate, hydrabamine, hydrobromide, hydrochloride, hydrogen phosphate, hydroiodide, hydroxynaphthoate, iodide, isethionate, itaconate, lactate, lactobionate, laurate, malate, maleate, mandelate, mesylate, methylbromide, methyinitrate, methylsulfate, monopotassium maleate, mucate, napsylate, nitrate, N-methylglucamine, oxalate, oxaloacetate, pamoate (embonate), palmate, palmitate, pantothenate, phosphate/diphosphate, piruvate, polygalacturonate, propionate, saccharate, salicylate, stearate, subacetate, succinate, sulfate, tannate, tartrate, teoclate, tosylate, triethiodide, trifluoroacetate and valerate. Preferred salts prepared according to the present invention include the succinate, glutarate and hemisulfate salts.

Those skilled in the art of organic chemistry will appreciate that many organic compounds can form complexes with solvents in which they are reacted or from which they are precipitated or crystallized. These complexes are known as "solvates". For example, a complex with water is known as a "hydrate". Solvates are within the scope of the invention. This invention includes within its scope stoichiometric hydrates as well as compounds containing variable amounts of water.

When used herein, the term "prodrug" means a compound which is converted within the body, e.g. by hydrolysis in the blood, into its active form that has medical effects. Pharmaceutically acceptable prodrugs are described in T. Higuchi and V. Stella, Prodrugs as Novel Delivery Systems, Vol. 14 of the A.C.S. Symposium Series, Edward B. Roche, ed.; Bioreversible Carriers in Drug Design, American Pharmaceutical Association and Pergamon Press, 1987; and in D. Fleisher, S. Ramon and H. Barbra "Improved oral drug delivery: solubility limitations overcome by the use of prodrugs", Advanced Drug Delivery Reviews (1996) 19(2) 115-130, each of which are incorporated herein by reference.

Prodrugs are any covalently bonded carriers that release the compound in vivo when such prodrug is administered to a patient Prodrugs are generally prepared by modifying functional groups in a way such that the modification is cleaved, either by routine manipulation or in vivo, yielding the parent compound. Prodrugs include, for example, compounds wherein the amine group is bonded to any group that, when administered to a patient, cleaves to form the amine group. Thus, representative examples of prodrugs include (but are not limited to) acetate, formate and benzoate derivatives of the amine functional group.

When used herein, the term "alkyl" refers to straight and branched groups containing up to six carbon atoms. Examples of such groups include methyl, ethyl, propyl, isopropyl, n-butyl, isobutyl, tert-butyl, pentyl or hexyl.

When used herein, the term "aryl" refers to, unless otherwise defined, single or fused aromatic rings suitably containing from 4 to 7, preferably 5 or 6, ring atoms in each ring. A fused ring system may include aliphatic rings and need only include one aromatic ring. Examples of suitable aryl rings include phenyl and naphthyl.

When used herein, the term "alkanol" refers to $C_{1-9}$alkyl alcohols, for example methanol, ethanol, industrially methylated spirit (IMS), n-propanol, iso-propanol (IPA), n-butanol, pentanol, hexanol, heptanol, octanol or nonanol, in particular methanol, ethanol, IMS, IPA or n-butanol.

The invention is illustrated by the following Examples.

EXAMPLES

HPLC was carried out using the following conditions:
Luna 3μm C18 50mm×2.0 mm Reverse Phase Column
Solvent A=Water/0.05% TFA
Solvent B=Acetonitrile/0.05% TFA
Gradient profile, 0.00 min=0% Solvent B; 8.00 min=95% Solvent B
Flow rate=1.0 ml/min
Temperature=40° C.
Injection Volume=1.0 μl

Example 1

DADCP (2,5-diamino-4,6-dichloropyrimidine) (400 g, 1.0 eq), [(1S,4R)+amino-2-cyclopenten-1-yl]methanol hydrochloride (aminoalcohol.HCl) (336 g, 1.0 eq), sodium bicarbonate (644 g, 3.5 eq) and n-butanol (3.2 L) were heated together at 95-100° C. for 8 h. The mixture was diluted with n-butanol 6.8 L, cooled to 75-80° C. and inorganics were removed by filtration. The cake was washed with n-butanol (2×600 ml).

The combined filtrate was concentrated down to ca 4 L then diluted with n-butanol (2.4 L). Triethylorthoformate (368 ml, 1.2 eq) and catalytic sulfuric acid (4 ml, 0.05 eq) were added and the mixture was heated at 65-70° C. for 6 h.

Cyclopropylamine (648 ml, 4.2 eq) was added at about 40-45° C. and the mixture was heated at 65-70° C. for 5 h. The reaction mixture was cooled to 20-25° C. then anhydrous sodium carbonate (480 g, 2 eq) was added and the slurry stirred for 1 h. The inorganics were removed by filtration and the cake washed with butanol (2×800 ml). The filtrate was concentrated to ca 7.5 L to remove excess cyclopropylamine then heated to 110-115 C. A solution of glutaric acid (296 g) in butanol (2 L) was added over 5 mins keeping the temp >105° C. Cooled to 100-105° C. then seeded with authentic abacavir glutarate. The resultant slurry was allowed to cool to 2-5° C. over at least 2 h, then aged @ 2-5° C. for 18 h. The product was collected by vacuum filtration, the cake washed with cold IPA (3×800 ml) and dried in-vacuo at 50° C. to give abacavir glutarate (82%, purity by HPLC 98.0% a/a). LCMS MH+ 287, retention time 2.46 min.

Example 2

DADCP (1 wt, 1.0 eq), [(1S,4R)-4-amino-2-cyclopenten-1-yl]methanol hydrochloride (aminoalcohol.HCl) (0.88 wt, 1.05 eq), sodium bicarbonate (1.17 wt, 2.5 eq) and n-butanol (6 vol) were heated together at 95-100° C. for ca 10 h. The reaction mixture was sampled for analysis by generic LC (complete when residual DADCP <0.5% a/a @ 220 nm). The mixture was diluted with butanol (10 vol), then cooled to 85-90° C. and the inorganics were removed by filtrabon. The hot filtrate (>70° C.) was passed through a jacketed Cuno filter containing Charcoal (Norit A Supra Eur, 0.04 wt). The cake was washed with hot n-butanol (2×2 vols) ensuring that the temp >70° C.

The combined filtrate was concentrated down to ca 8 vols by vacuum distillation to remove water (collected ca. 12 vols), the temperature adjusted to 65-70° C. then triethylorthoformate (1.01 vol, 1.1 eq) and sulfuric acid (0.01 vol, 0.05 eq) were added. The mixture was heated at 65-70° C. for 3 h then sampled for analysis by generic LC.

The reaction mixture was cooled to 45-50° C., cyclopropylamine (1.62 vol, 4.2 eq) was added and the mixture heated up to 85-90° C. at which it was stirred for 2 h. The reaction mixture was sampled for analysis by generic LC (complete when residual chloropurine <0.5% a/a @ 220 nm). Butanol (4 vol) was added and the reaction was concentrated to ca 7.5 vols to remove excess cyclopropylamine (diluted and repeated as necessary), diluted with butanol (10 vol) then heated to 75-80° C. A solution of glutaric acid (0.74 wt) in butanol (5 vol) was heated to 75° C. and was added over 5 mins keeping the temp >75° C. Seeded with authentic abacavir glutarate and the resultant slurry was allowed to cool to 2-5° C. over at least 2 h, then aged @ 2-5° C. for at least 1 h. The product was collected by vacuum filtration, the cake washed with cold IPA (1×4 vol then 2×3 vol) and dried in-vacuo at 50° C. to give abacavir glutarate (85%, purity by HPLC 98.7% a/a). LCMS MH+ 287, retention time 2.46 min.

The invention claimed is:

1. A process for preparing a chloropurine compound of formula (I)

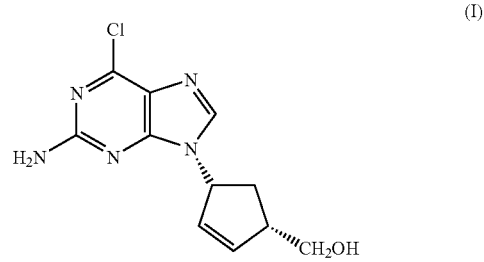

which comprises ring closure of a compound of formula (VII)

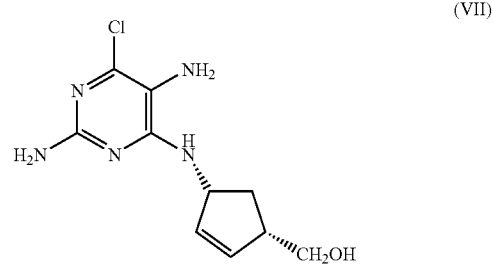

in the presence of a catalytic amount of acid and at least one equivalent of a trialkylorthoformate.

2. A process according to claim 1 wherein the acid is sulfuric acid, hydrochloric acid, or an alkyl or arylsulfonic acid.

3. A process according to claim 1 wherein the acid is present in an amount of from 0.05 to 0.1 equivalents by mole based on an amount of the compound of formula (VII).

4. A process according to claim 1 wherein the trialkylorthoformate is triethylorthoformate.

5. A process according claim 1 wherein the trialkylorthoformate is present in an amount of 1 to 1.5 equivalents by mole based on the amount of the compound of formula (VII).

6. A process according to claim 1 wherein the compound of formula (VII) is prepared by condensing an amino alcohol of formula (IV)

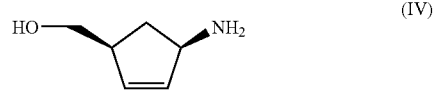

with a compound of formula (VIII)

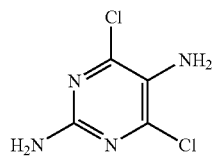

(VIII)

in the presence of a base.

7. A process according to claim 6 wherein the condensation reaction is carried out in n-butanol in the presence of sodium bicarbonate.

8. A process according to claim 1 wherein the condensation reaction is carried out in n-butanol in the presence of anhydrous potassium carbonate.

9. A process according to claim 1 wherein the chloropurine compound of formula (I) prepared by the ring closure reaction is converted in situ to abacavir.

* * * * *